United States Patent
Schaffer

(10) Patent No.: US 10,226,599 B2
(45) Date of Patent: Mar. 12, 2019

(54) INFLATABLE MEDICAL DEVICE AND RELATED SHEATH

(71) Applicant: C.R. BARD, INC., Murray Hill, NJ (US)

(72) Inventor: Andrew Schaffer, Gilbert, AZ (US)

(73) Assignee: C.R. BARD, INC., Murray Hill, NJ (US)

( * ) Notice: Subject to any disclaimer, the term of this patent is extended or adjusted under 35 U.S.C. 154(b) by 256 days.

(21) Appl. No.: 14/757,718

(22) Filed: Dec. 23, 2015

(65) Prior Publication Data

US 2016/0175565 A1 Jun. 23, 2016

Related U.S. Application Data

(60) Provisional application No. 62/096,294, filed on Dec. 23, 2014.

(51) Int. Cl.
*A61M 25/10* (2013.01)

(52) U.S. Cl.
CPC . *A61M 25/1002* (2013.01); *A61M 2025/1081* (2013.01); *A61M 2025/1084* (2013.01); *A61M 2025/1097* (2013.01)

(58) Field of Classification Search
CPC .............. A61M 25/10; A61M 25/1002; A61M 25/1011; A61M 25/104; A61M 2025/1004; A61M 2025/1045; A61M 2025/1047; A61M 2025/107; A61M 2025/1072; A61M 2025/1075; A61M 2025/1081; A61M 2025/1084; A61M 2025/1095; A61M 2025/1097
See application file for complete search history.

(56) References Cited

U.S. PATENT DOCUMENTS

| | | | | |
|---|---|---|---|---|
| 4,183,102 A | * | 1/1980 | Guiset | A61F 2/82 604/101.01 |
| 4,447,227 A | * | 5/1984 | Kotsanis | A61B 17/0218 604/908 |
| 4,641,653 A | * | 2/1987 | Rockey | A61F 5/00 604/909 |
| 4,763,653 A | * | 8/1988 | Rockey | A61B 17/12 604/103.07 |
| 4,909,252 A | * | 3/1990 | Goldberger | A61M 25/1002 604/103.1 |
| 5,019,042 A | | 5/1991 | Sahota | |
| 5,049,131 A | * | 9/1991 | Deuss | A61M 25/1002 604/103.02 |
| 5,078,685 A | * | 1/1992 | Colliver | A61M 25/104 604/103.07 |
| 5,108,370 A | * | 4/1992 | Walinsky | A61M 25/104 604/102.02 |

(Continued)

*Primary Examiner* — Ryan J Severson
(74) *Attorney, Agent, or Firm* — King & Schickli, PLLC

(57) ABSTRACT

An inflatable balloon is provided. The balloon includes a central lumen open at both ends of the balloon and connected to a gap formed in one sidewall of the balloon. This arrangement may provide the balloon with a generally C-shaped profile with the open central lumen within the balloon along a center axis thereof, such as to allow for perfusion. The balloon may also include an inflation port offset from a central axis and a shaft including an inflation lumen connected to the inflation port. A sheath may also be provided with a window through which the balloon may project in use.

12 Claims, 5 Drawing Sheets

(56) References Cited

U.S. PATENT DOCUMENTS

| | | | | |
|---|---|---|---|---|
| 5,308,356 | A | 5/1994 | Blackshear, Jr. et al. | |
| 5,330,528 | A * | 7/1994 | Lazim | A61F 2/07 606/194 |
| 5,388,590 | A * | 2/1995 | Horrigan | A61M 25/0169 600/435 |
| 5,395,333 | A * | 3/1995 | Brill | A61M 25/1011 604/101.05 |
| 5,401,241 | A * | 3/1995 | Delany | A61M 25/0041 604/103.07 |
| 5,403,280 | A | 4/1995 | Wang | |
| 5,423,851 | A * | 6/1995 | Samuels | A61F 2/07 606/108 |
| 5,433,706 | A * | 7/1995 | Abiuso | A61M 25/1002 604/101.01 |
| 5,470,314 | A * | 11/1995 | Walinsky | A61M 25/1002 604/103.11 |
| 5,484,411 | A | 1/1996 | Inderbitzen et al. | |
| 5,554,119 | A * | 9/1996 | Harrison | A61M 25/1002 604/101.05 |
| 5,556,382 | A | 9/1996 | Adams | |
| 5,558,642 | A * | 9/1996 | Schweich, Jr. | A61M 25/1002 604/101.05 |
| 5,613,948 | A * | 3/1997 | Avellanet | A61M 25/1002 604/103.07 |
| 5,716,340 | A * | 2/1998 | Schweich, Jr. | A61M 25/1002 604/101.05 |
| 5,720,723 | A * | 2/1998 | Adams | A61M 25/104 604/103.01 |
| 5,749,852 | A * | 5/1998 | Schwab | A61M 25/1002 604/103.01 |
| 5,759,172 | A * | 6/1998 | Weber | A61M 25/1002 604/103.07 |
| 5,836,957 | A * | 11/1998 | Schulz | A61B 17/320783 604/103.07 |
| 5,954,740 | A * | 9/1999 | Ravenscroft | A61M 25/1002 604/103.07 |
| 5,961,490 | A * | 10/1999 | Adams | A61M 25/104 604/103.03 |
| 6,110,192 | A * | 8/2000 | Ravenscroft | A61M 25/1002 604/103.08 |
| 6,139,517 | A * | 10/2000 | Macoviak | A61M 25/1002 604/101.05 |
| 6,183,492 | B1 * | 2/2001 | Hart | A61B 17/12036 604/96.01 |
| 6,190,356 | B1 | 2/2001 | Bersin | |
| 6,254,563 | B1 * | 7/2001 | Macoviak | A61M 25/1011 604/101.05 |
| 6,562,056 | B2 * | 5/2003 | Jervis | A61B 17/00234 600/207 |
| 6,565,589 | B1 * | 5/2003 | Jervis | A61B 17/00234 604/96.01 |
| 6,679,860 | B2 | 1/2004 | Stiger | |
| 6,695,864 | B2 * | 2/2004 | Macoviak | A61M 25/1002 606/194 |
| 6,764,484 | B2 | 7/2004 | Richardson et al. | |
| 7,163,524 | B2 | 1/2007 | Ishii | |
| 7,534,223 | B2 | 5/2009 | Boutilette et al. | |
| 7,559,923 | B2 * | 7/2009 | Seward | A61B 17/3478 604/506 |
| 7,686,783 | B2 * | 3/2010 | Jenson | A61B 17/22 604/104 |
| 8,323,242 | B2 * | 12/2012 | Beckham | A61M 25/104 604/103.06 |
| 9,421,056 | B2 * | 8/2016 | O'Neil | A61M 29/02 |
| 9,446,222 | B2 * | 9/2016 | Silvestro | A61M 29/02 |
| 9,592,119 | B2 * | 3/2017 | Tilson | A61F 2/2433 |
| 2002/0010411 | A1 * | 1/2002 | Macoviak | A61M 25/1002 604/8 |
| 2002/0032456 | A1 * | 3/2002 | Jervis | A61B 17/00234 606/190 |
| 2002/0161388 | A1 * | 10/2002 | Samuels | A61L 29/085 606/192 |
| 2003/0004462 | A1 * | 1/2003 | Halpin | A61B 17/0057 604/99.04 |
| 2005/0123702 | A1 * | 6/2005 | Beckham | A61M 25/104 428/36.3 |
| 2007/0067010 | A1 * | 3/2007 | Wang | A61M 25/1002 623/1.11 |
| 2007/0185443 | A1 * | 8/2007 | Euteneuer | A61M 25/1002 604/96.01 |
| 2007/0185444 | A1 * | 8/2007 | Euteneuer | A61M 25/1002 604/96.01 |
| 2008/0243066 | A1 * | 10/2008 | Jenson | A61B 17/22 604/99.01 |
| 2009/0088789 | A1 * | 4/2009 | O'Neil | A61M 29/02 606/192 |
| 2010/0179581 | A1 * | 7/2010 | Beckham | A61M 25/104 606/192 |
| 2011/0144742 | A1 | 6/2011 | Madrid et al. | |
| 2013/0190796 | A1 * | 7/2013 | Tilson | A61F 2/2433 606/192 |
| 2015/0250991 | A1 * | 9/2015 | Silvestro | A61M 29/02 606/194 |
| 2015/0272732 | A1 * | 10/2015 | Tilson | A61M 25/1002 623/2.11 |
| 2015/0320330 | A1 * | 11/2015 | Sparks | A61N 1/057 600/375 |
| 2016/0045240 | A1 * | 2/2016 | O'Neil | A61M 29/02 623/17.12 |
| 2016/0175565 | A1 * | 6/2016 | Schaffer | A61M 25/1002 606/194 |
| 2016/0235531 | A1 * | 8/2016 | Ciobanu | A61F 2/2427 |
| 2016/0331362 | A1 * | 11/2016 | O'Neil | A61M 29/02 |

* cited by examiner

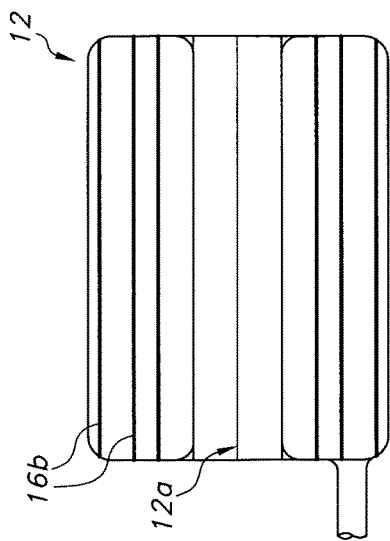
FIG. 5
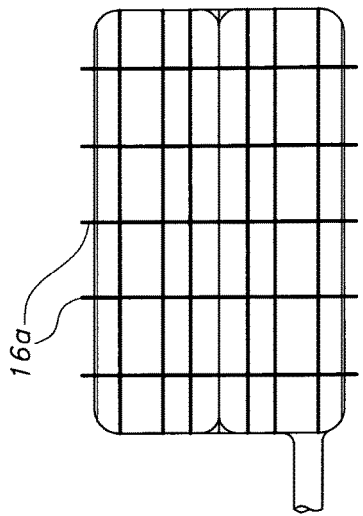
FIG. 7
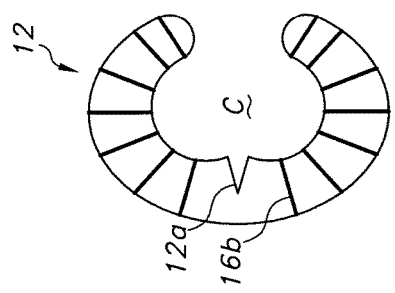
FIG. 4
FIG. 6

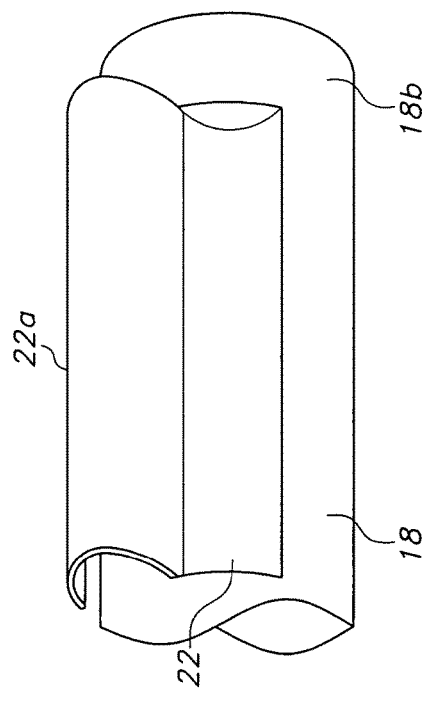
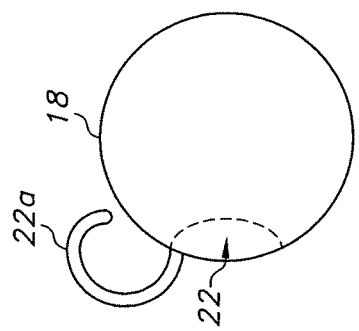
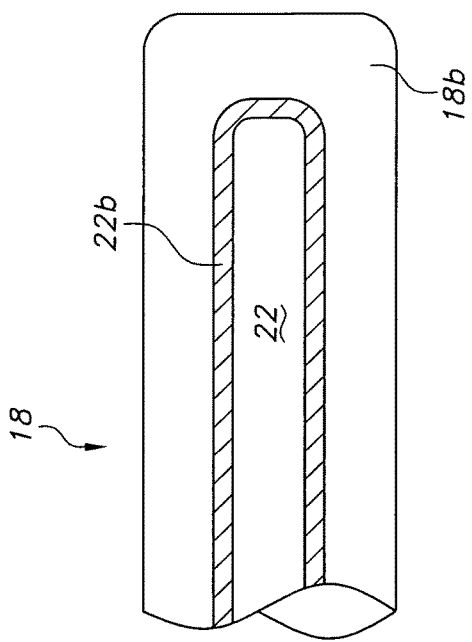

INFLATABLE MEDICAL DEVICE AND RELATED SHEATH

This application claims the benefit of U.S. Provisional Patent Application Ser. No. 62/096,294, the disclosure of which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND

1. Technical Field

Inflatable medical devices, sheaths, and methods for making and using the same are disclosed. More narrowly, medical balloons, such as those used for dilatation, are disclosed, as is a sheath for use with a medical balloon.

2. Description of Related Art

Inflatable structures, such as balloons, are widely used in medical procedures. A balloon is inserted, typically on the end of a catheter, until the balloon reaches the area of interest. Adding pressure to the balloon causes the balloon to inflate. In one variation of use, the balloon creates a space inside the body when the balloon inflates.

Balloons may be used in the heart valves, including during Balloon Aortic Valvuloplasty (BAV) and Transcatheter Aortic Valve Implantation (TAVI). The balloons can be used to open a stenosed aortic valve. A stenosed valve may have hard calcific lesions which may tend to tear or puncture a balloon. Additionally, a precise inflated balloon diameter may be desired for increased safety and control.

The high fluid pressures exerted by the heart, combined with the normal pulsation of the opening and closing valves, pose a very dynamic environment for balloon angioplasty. When the balloon is inflated across the valve, the forces tend to squeeze the balloon and create a phenomenon called "ejection," which causes the balloon to slip out of the valve. The clinician then has to deflate the balloon, reposition it, and re-inflate it, which can prolong the procedure. The inability to dilate the valve properly can also lead to a failed procedure, and lead to alternate, potentially less desirable treatment regimes.

Accordingly, a need is identified for a device to solve the ejection problem. The device would be able to be anchored during inflation, such that valve fluctuations do not eject the balloon from the valve. The device would also be adapted to use perfusion to allow blood flow through the inflated balloon, which provides the added benefit of allowing the blood to circulate normally during longer inflation cycles.

SUMMARY

An inflatable medical device is provided that is adapted to use perfusion to allow blood flow through the inflated balloon, which provides the added benefit of allowing the blood to circulate normally during longer inflation cycles. The device includes a balloon with a generally C-shaped profile. A corresponding sheath includes a window through which a portion of the balloon may project on inflation. Once deflated, the balloon may be rolled onto an associated catheter shaft with the aid of the sheath.

According to a more specific aspect of the disclosure, an apparatus for performing a medical procedure in the vasculature includes an inflatable balloon having a generally C-shaped profile providing the balloon with an open central lumen. The balloon includes a convex side and a concave side having a notch forming a part of the open central lumen. The proximal end of the balloon includes an inflation port, and a catheter shaft connected to the balloon has a first axis offset from the central lumen of the balloon.

Reinforcements, such as fibers, may also be wrapped around the balloon. This may include at least one fiber wrapped around the balloon in an axial direction. At least one fiber may be wrapped around the balloon in a circumferential direction.

The apparatus may also comprise a sheath having a window through which a portion of the balloon may project. The sheath may be connected to a first outer shaft and the balloon is connected to a second, inner shaft adapted for moving within the first outer shaft, the second, inner shaft including an inflation lumen for inflating the balloon. The first outer shaft may include a first hub and the second, inner shaft includes a second hub positioned proximal of the first hub.

A further aspect of the disclosure pertains to an apparatus for performing a medical procedure in the vasculature. The apparatus comprises an inflatable balloon and a sheath for at least partially covering the balloon. The sheath includes a window through which at least a portion of the balloon may pass.

In one embodiment, the window extends in a circumferential direction and a longitudinal direction of the sheath. The sheath includes a reinforcement adjacent to the window. A corresponding dimension of the window in the axial direction is greater than a length of the balloon, which may be generally C-shaped so as to provide the balloon with a central lumen.

The sheath may be connected to a first outer shaft and the balloon connected to a second, inner shaft adapted for moving within the first outer shaft. The second, inner shaft includes an inflation lumen for inflating the balloon. The first outer shaft may include a first hub and the second, inner shaft has a second hub positioned proximal to the first hub.

Still a further aspect of the disclosure pertains to an apparatus for performing a medical procedure in the vasculature. The apparatus comprises an inflatable balloon having a central lumen open at both ends of the balloon and connected to a gap formed in one sidewall of the balloon. The balloon may have a substantially C-shaped cross-section.

Yet a further aspect of the disclosure pertains to an apparatus for performing a medical procedure in the vasculature. The apparatus comprises an inflatable balloon having a generally C-shaped profile providing the inflatable balloon with an open central lumen. The inflatable balloon includes an interior compartment in communication with an inflation port. A catheter shaft includes an inflation lumen for communicating with the inflation port, the catheter shaft extending at least partially into an interior compartment of the balloon. Hence, the balloon may be wrapped around the shaft. The balloon may include an upper lobe and a lower lobe, the inflation port being provided in one of the upper or lower lobes.

Still another aspect of the disclosure pertains to a method of deploying a medical balloon. The method comprises providing a sheath including a window, and inflating the balloon through a shaft such that the balloon passes at least partially through the window of the sheath. The method may further include the steps of: (1) deflating the balloon; and (2) wrapping the balloon around the shaft.

BRIEF DESCRIPTION OF THE DRAWING FIGURES

The accompanying drawing figures incorporated herein and forming a part of the specification illustrate several aspects of the adjustable support and together with the description serve to explain certain principles thereof.

FIG. 4 is a side view of another embodiment of the inflatable device;

FIG. 5 is a front view of the embodiment of FIG. 4;

FIG. 6 is a side view of another embodiment of the inflatable device;

FIG. 7 is a front view of the embodiment of FIG. 6;

FIGS. 15-17 are different views of various reinforcements for associating with the sheath to facilitate retraction of the inflatable device.

Reference will now be made in detail to the present preferred embodiments of the aspects of the disclosure, examples of which are illustrated in the accompanying drawing figures.

DETAILED DESCRIPTION

Figure 2:
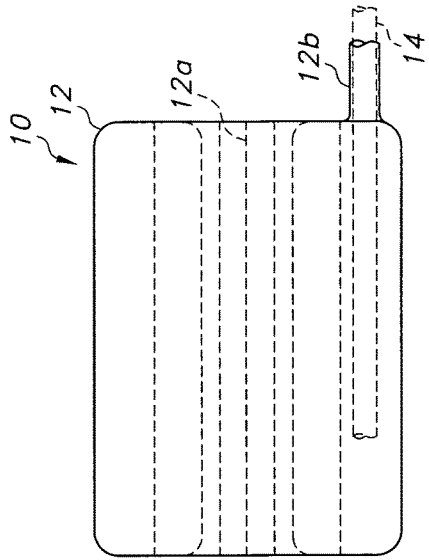
FIG. 2 is a rear view of the inflatable device of FIG. 1.
Figure 3:
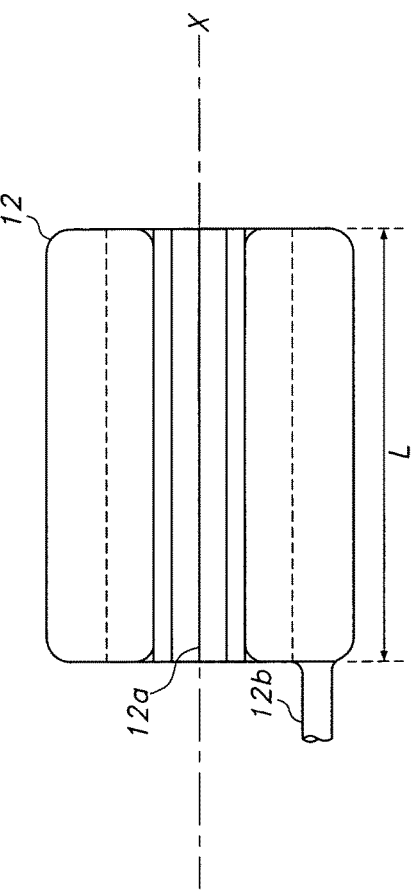
FIG. 3 is a front view of the inflatable device of FIG. 1.
Figure 1:
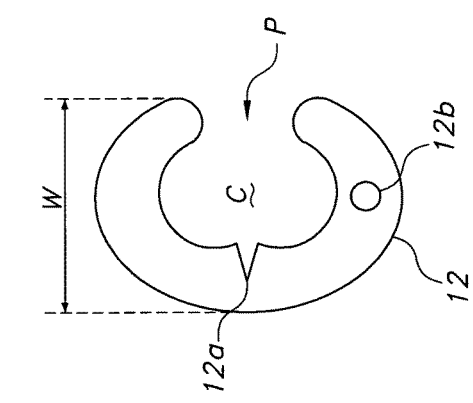
FIG. 1 is an end, view of an inflatable device according to one aspect of the disclosure.

FIGS. 1-3 illustrate one embodiment of an inflatable medical device 10 according to the present disclosure. FIG. 1 illustrates an inflatable portion of the device 10, which may be considered as a balloon 12. In the illustrated embodiment, the balloon 12 has a length L that is substantially greater than its width W. Thus, the balloon 12 is considered to be elongated as indicated in FIG. 3. However, it is possible for the balloon 12 to have a shorter length L.

As can be appreciated from FIG. 1, the balloon 12 includes a gap P in one side in communication with a central lumen C. Hence, in this embodiment, the balloon 12 is considered to be generally C-shaped in profile, such as when viewed from the longitudinal direction (that is, each cross-section of the balloon along its length is generally C-shaped and substantially identical, without any twisting). Thus, the balloon 12 may be considered to have a concave inner surface and a convex outer surface. Alternatively, without deviating from the meaning of the term C-shaped, the balloon 12 may be considered to have two closed ends or lobes (upper and lower) in a single cross-section, with the closed ends either touching each other or opposing to form a gap in fluid communication with central lumen C.

For purposes of reducing stress, the balloon 12 may be provided with a relief structure, such as a notch 12a. The notch 12a may be along the concave inner surface of the balloon 12. The arrangement may be such that the notch 12a may partially or fully compress when the balloon 12 is in a configuration where the closed ends are touching (compare FIGS. 1 and 8).

As also shown in FIGS. 2 and 3, the balloon 12 further includes an inflation port 12b for receiving an inflation fluid, such as a saline solution. The port 12b may be a single port attached to a catheter shaft 14 providing an inflation lumen I for supplying the fluid. As can be appreciated, the axis of the port 12b is offset from the central lumen C, which is generally aligned with a center axis X. In the illustrated embodiment, the port 12b is connected to a lower lobe of the C-shaped balloon 12, but could also be associated with the upper lobe as well, or provided between the upper and lower lobes.

The shaft 14 may be connected to the port 12b external to the interior of the balloon 12, and/or may pass through the port 12b into the balloon interior, including to the distal end thereof. Hence, the shaft 14 in this embodiment is offset from the central axis X as well.

The balloon 12 may be manufactured (prior to association with the shaft 14) using a vacuum-pressure mold and a parison, or by using water soluble mandrels (see, e.g., U.S. Patent Application Publication No. 20130190796). The balloon 12 may be formed of two C-shaped parts or halves connected together, or may be formed from an elongated tubular structure molded into a C-shaped configuration.

Figure 8:
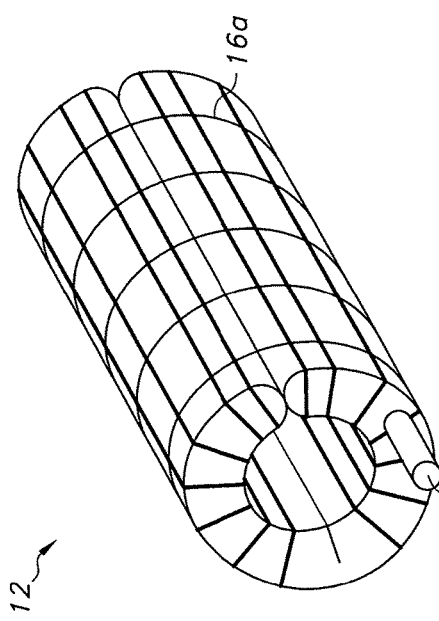
FIG. 8 is a perspective view of the embodiment of FIG. 6.

As indicated in FIGS. 4-8, one or more reinforcements, such as fibers 16, may also be wrapped around the formed balloon 12 to support the intended shape when inflated. For example, as shown in FIGS. 6, 7, and 8, circumferential fibers 16a may be wrapped around the balloon 12 to collapse the C-shape into an annulus (i.e., the notch 12a substantially disappears, but the balloon 12 remains circumferentially discontinuous), while longitudinal fibers 16b may be used to retain the shape in the opposite direction. The fibers 16a, 16b may be continuous or discontinuous, and may be applied in any arrangement as long as the shape-retaining function is provided. The fibers 16a, 16b may be inelastic or elastic.

Figure 9:
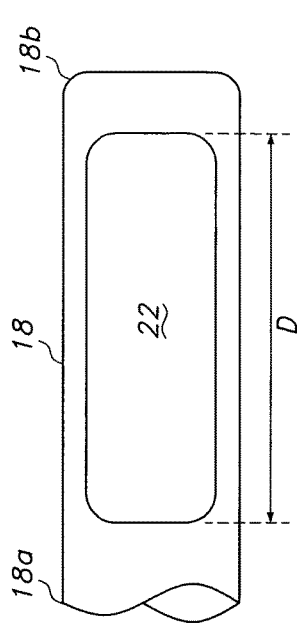
FIG. 9 is a cutaway top view of a sheath for possible use in connection with the inflatable device.
Figure 11:
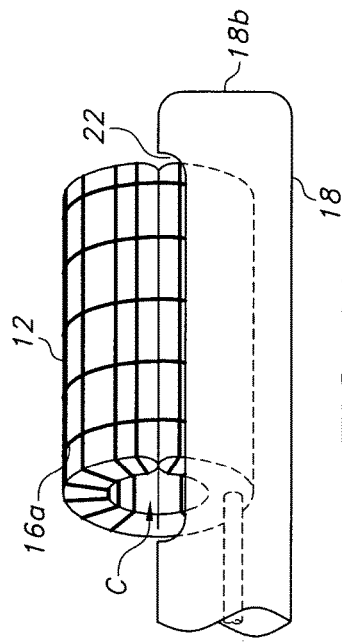
FIG. 11 is a side view of the inflatable device of FIG. 6 in combination with the sheath.
Figure 10:
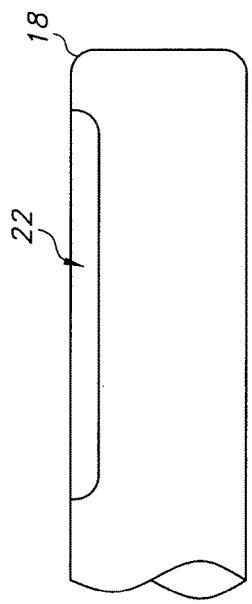
FIG. 10 is a cutaway side view of the sheath.
Figure 12:
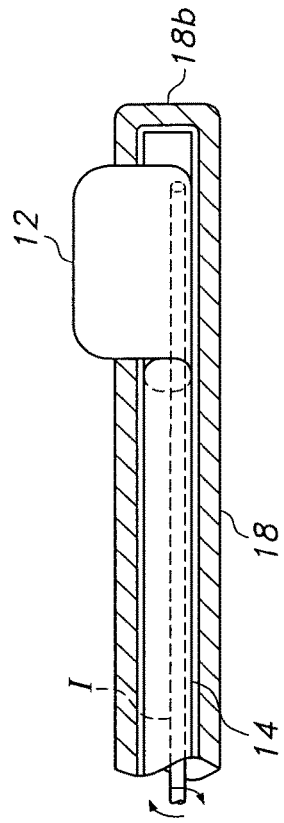
FIG. 12 is a side cross-sectional view illustrating an inflatable device projecting through a window in the sheath.
Figure 13:
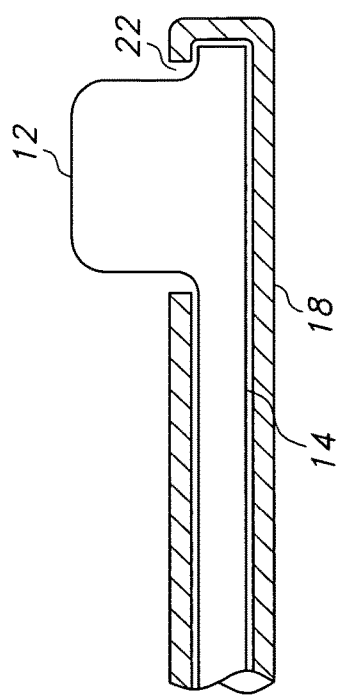
FIG. 13 is a top cross-sectional view illustrating the rolling up of the inflatable device within the sheath.

Referring now to FIGS. 9-17, the device 10 may be used in connection with an outer sheath 18 for receiving the balloon 12 connected to the shaft 14 (the two structures together could be considered to form a single device for purposes of this disclosure). The sheath 18 may include a proximal portion 18a adapted for being attached to a support shaft 20, and a distal portion 18b including a window 22. The window 22 may be elongated and formed in a sidewall of the sheath, as shown in FIGS. 9 and 10. The sheath 18 may have a closed end at the distal portion 18b.

The inner diameter of the sheath 18 and shaft 20 is such that the balloon 12 in the deflated condition may be delivered to a position in alignment with the window 22. The window 22 may have a longitudinal dimension D at least as great as the length L of the balloon 12 (see FIG. 9). The entire length of the sheath 18 is thus greater than the length of the balloon 12.

In use, the balloon 12 may be positioned in alignment with the window 22, and in a configuration where it is folded or wrapped around the shaft 14 extending into the interior compartment of the balloon. On inflation (and, in the case where it is wrapped, unfurling via rotation of the shaft 14), a portion of the balloon 12 may thus emerge and project from the window 22 (FIG. 12) in order to provide a treatment in the vasculature, such as by causing dilatation. Alternatively, the entire balloon 12 may be passed through the window 22 prior to inflation, and then partially or fully inflated. The balloon 12 may be the C-shaped balloon noted above, or else may take a different form, with a preference for those balloons having perfusion capabilities.

In any case, it can be appreciated, the central lumen C of the balloon 12 allows for blood to continue flowing, including along the center axis X, during inflation. In the situation where the balloon 12 remains associated with the sheath 18, it can also be appreciated that the opening provided by the window 22 helps to anchor the balloon 12 in position in order to help prevent undesirable ejection. Continuous perfusion may be provided via the central lumen C despite the full or partial inflation of the balloon 12 in a C-shaped form, as can be appreciated from FIG. 1.

Upon deflation of the balloon 12, the sheath 18 can also be used to assist in refolding of the balloon 12. Specifically, once deflated, the shaft 14 supporting the balloon 12 may be rotated (FIG. 13), which shaft may include the inflation lumen I and may pass into the interior compartment of the balloon. In view of the offset positioning of the shaft 14, this rotation would tend to urge the balloon 12 against the lip of the distal end portion 18*b* of the sheath 18 bounding the window 22. This helps to roll the balloon 12 to a wrapped configuration around the shaft 14, such that it may be withdrawn.

Figure 14:
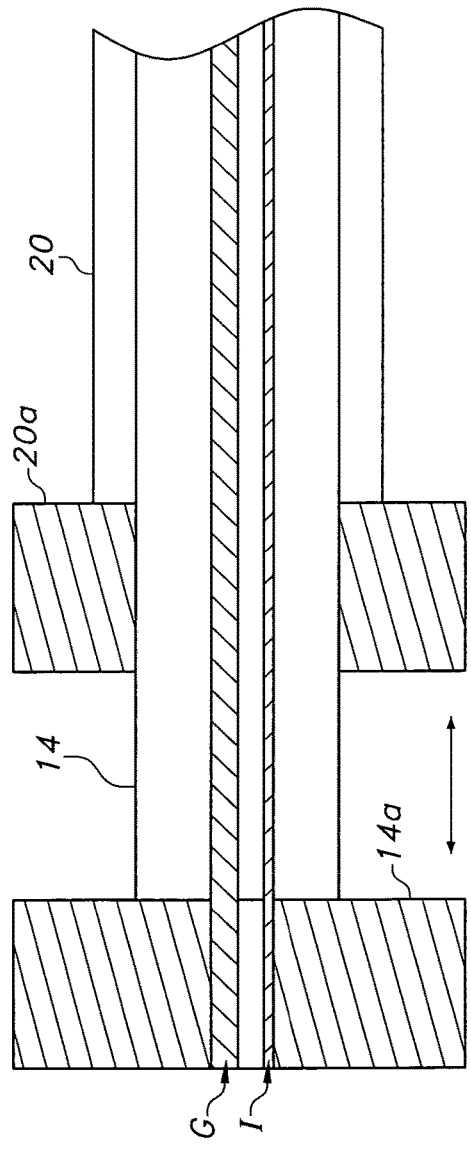
FIG. 14 is a partially cutaway, partially cross-sectional view of a hub assembly.

In order to facilitate the relative rotation within the outer shaft 20 associated with the sheath 18, the inner shaft 14 may be slidably received within an outer hub 20*a*, as shown in FIG. 14. The inner shaft 14 may also include an inner hub 14*a* proximal to the outer hub 20*a*, and including the proximal end of the inflation lumen I and guidewire lumen G (if present).

As can be appreciated, the shaft 14 must be able to withstand a significant amount of torque in order to achieve this rewrapping of the balloon 12. Hence, it is possible to provide the shaft 14 with a reinforced configuration, such as by using braiding or hard polymers. As this may have a negative impact on trackability, it is possible to use the device with shorter working lengths with access sites near the heart (e.g., subclavian, jugular, transseptial, etc.). This may reduce the need for enhanced trackability.

It can be understood that the above-described configuration does not facilitate the passage of a guidewire through the shaft 14, as would be the case in a conventional "over-the-wire" configuration. Accordingly, delivery of the device 10 to a treatment site could be achieved through attachment of a wire external to the shaft 14 or balloon 12, similar to the situation in a "rapid exchange" configuration. Alternatively, a clinician could thread a wire through the central lumen C of the balloon 12, or attach a wire to the external sheath 18.

It can also be understood that the force required to roll the deflated balloon 12 back inside the sheath 18 may be significant, and could impart high stress on the surrounding structure forming the window 22. Accordingly, as shown in FIGS. 15-17, a reinforcement, such as a rounded lip or scroll 22*a*, may be provided to help ensure that the window 22 does not simply tear during the process. Alternatively or additionally, a reinforcement in the form of a frame 22*b*, such as made of a metal or hardened plastic, may be provided along all or a portion of the perimeter of the window 22 in order to provide enhanced strength and tear resistance.

The foregoing has been presented for purposes of illustration and description. It is not intended to be exhaustive or, to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled. Any elements described herein as singular can be pluralized (i.e., anything described as "orie" can be more than one), and plural elements can be used individually. Characteristics disclosed of a single variation of an element, the device, the methods, or combinations thereof can be used or apply for other variations, for example, dimensions, burst pressures, shapes, materials, or combinations thereof. Any species element of a genus element can have the characteristics or elements of any other species element of that genus. The term "comprising" is not meant to be limiting. The above-described configurations, elements or complete assemblies and methods and their elements for carrying out the invention, and variations of aspects of the invention can be combined and modified with each other in any combination.

The invention claimed is:

1. An apparatus for performing a medical procedure in the vasculature, comprising:
    an inflatable balloon having a generally C-shaped profile providing the balloon when inflated with an open lumen along a center axis;
    and
    a catheter shaft connected to the balloon, the balloon being wrapped around the shaft in a deflated condition.

2. The apparatus of claim 1, wherein the inflatable balloon includes a convex side and a concave side having a notch facing the open lumen.

3. The apparatus of claim 1, the catheter shaft having a central axis offset from the open lumen of the inflatable balloon and the center axis of the balloon.

4. The apparatus of claim 1, further including fibers wrapped around the inflatable balloon.

5. The apparatus of claim 1, further including at least one fiber wrapped around the balloon in an axial direction and at least one fiber wrapped around the inflatable balloon in a circumferential direction.

6. The apparatus of claim 1, further including a sheath having a window through which a portion of the inflatable balloon may project.

7. The apparatus of claim 6, wherein the sheath is connected to a first outer shaft and the catheter shaft is adapted for moving within the first outer shaft, the catheter shaft including an inflation lumen for inflating the inflatable balloon.

8. The apparatus of claim 7, wherein the first outer shaft includes a first hub and the catheter shaft includes a second hub positioned proximal of the first hub.

9. An apparatus for performing a medical procedure in the vasculature, comprising:
    an inflatable balloon having a generally C-shaped profile providing the inflatable balloon with an open central lumen when in an inflated condition, the inflatable balloon including an interior compartment in communication with an inflation port; and
    a catheter shaft including an inflation lumen for communicating with the inflation port, the catheter shaft extending at least partially into the interior compartment of the balloon,
    whereby the balloon is wrapped around the shaft when the balloon is in a deflated condition.

10. The apparatus of claim 9, wherein the inflatable balloon includes an upper lobe and a lower lobe, the inflation port being provided in one of the upper or lower lobes.

11. The apparatus of claim 9, wherein the catheter shaft extends at least partially into the interior compartment of the balloon along an offset axis relative to the open central lumen.

12. An apparatus for performing a medical procedure in the vasculature, comprising:
- an inflatable balloon having a generally C-shaped profile providing the inflatable balloon with an open lumen along a center axis and a port at a proximal end of the balloon in communication with a balloon interior; and
- a catheter shaft connected to the balloon, the shaft passing through the port into the balloon interior to a distal end of the inflatable balloon.

* * * * *